US012618752B2

(12) United States Patent
Taher et al.

(10) Patent No.: US 12,618,752 B2
(45) Date of Patent: May 5, 2026

(54) COLLECTING DEVICE AND A METHOD FOR COLLECTION OF AIRBORNE PARTICLES EXHALED BY A HUMAN BEING

(71) Applicant: IMEC VZW, Leuven (BE)

(72) Inventors: Ahmed Taher, Heverlee (BE); Benjamin Jones, Kessel-Lo (BE); Sophie Roth, Etterbeek (BE)

(73) Assignee: IMEC VZW, Leuven (BE)

( * ) Notice: Subject to any disclaimer, the term of this patent is extended or adjusted under 35 U.S.C. 154(b) by 390 days.

(21) Appl. No.: 18/288,501

(22) PCT Filed: Apr. 20, 2022

(86) PCT No.: PCT/EP2022/060428
§ 371 (c)(1),
(2) Date: Oct. 26, 2023

(87) PCT Pub. No.: WO2022/228967
PCT Pub. Date: Nov. 3, 2022

(65) Prior Publication Data
US 2024/0219272 A1 Jul. 4, 2024

(30) Foreign Application Priority Data

Apr. 26, 2021 (EP) .................................... 21170437

(51) Int. Cl.
*G01N 1/22* (2006.01)
*A61B 5/08* (2006.01)
*A61B 5/097* (2006.01)

(52) U.S. Cl.
CPC .......... *G01N 1/2208* (2013.01); *A61B 5/082* (2013.01); *A61B 5/097* (2013.01); *G01N 1/2214* (2013.01);
(Continued)

(58) Field of Classification Search
CPC .. G01N 1/2208; G01N 1/2214; G01N 1/2273; G01N 1/22; G01N 2001/2217;
(Continued)

(56) References Cited

U.S. PATENT DOCUMENTS

| | | | | | |
|---|---|---|---|---|---|
| 5,304,125 | A | * | 4/1994 | Leith ................. | A61M 15/0086 |
| | | | | | 128/200.14 |
| 6,101,886 | A | * | 8/2000 | Brenizer .............. | G01N 1/2205 |
| | | | | | 73/863.25 |

(Continued)

FOREIGN PATENT DOCUMENTS

| | | | |
|---|---|---|---|
| WO | WO-2017/001374 A1 | 1/2017 | |
| WO | WO-2018/126119 A1 | 7/2018 | |

(Continued)

OTHER PUBLICATIONS

Maldonado-Garcia, et al: "Chip-Scale Aerosol Impactor with Integrated Resonant Mass Balances for Real Time Monitoring of Airborne Particulate Concentrations", 28th IEEE International Conference on Micro Electro Mechanical Systems (MEMS), pp. 885-888, 2015.

(Continued)

*Primary Examiner* — Frank M Lawrence, Jr.
(74) *Attorney, Agent, or Firm* — MOSER TABOADA

(57) ABSTRACT

A collecting device (200) for collecting airborne particles comprises: a first (202) and second layer (220) spaced apart for forming a particle collection chamber (240; 340) therebetween: wherein inlets (210; 310) and outlets (230; 330) are configured for transporting a flow of air (104) into and out of the particle collection chamber (240; 340) and configured for allowing capturing airborne particles by impaction. The collecting device (200) further comprises at least one liquid access port (260; 260a, 260b; 360a-360h) for filling the particle collection chamber (240; 340) with a reagent; and wherein the particle collection chamber (240;

(Continued)

340) comprises at least one side wall (246; 346) for defining flow of the reagent, such that a first portion (248a; 348a) and a second portion (248b; 348b) of the particle collection chamber (240; 340) are arranged on opposite sides of the at least one side wall (246; 346).

14 Claims, 5 Drawing Sheets

(52) U.S. Cl.
CPC ... *G01N 1/2273* (2013.01); *G01N 2001/2217* (2013.01); *G01N 2001/2223* (2013.01)

(58) Field of Classification Search
CPC .. G01N 2001/2223; A61B 5/082; A61B 5/097
USPC .............. 96/413; 73/863.22, 863.41, 864.51, 73/864.57, 864.72, 23.3
See application file for complete search history.

(56) References Cited

U.S. PATENT DOCUMENTS

| | | | |
|---|---|---|---|
| 7,135,060 B2 * | 11/2006 | Jordan, Sr. ............. | B01D 45/10 55/435 |
| 7,631,567 B1 | 12/2009 | Hill | |
| 2004/0118222 A1 | 6/2004 | Cornish et al. | |
| 2005/0279181 A1 | 12/2005 | Trakumas et al. | |
| 2007/0173731 A1 | 7/2007 | Meka et al. | |
| 2008/0061238 A1 | 3/2008 | Hok et al. | |
| 2009/0275113 A1 | 11/2009 | Maltezos et al. | |
| 2010/0062415 A1 | 3/2010 | Schwoebel et al. | |
| 2010/0268106 A1 | 10/2010 | Johnson et al. | |
| 2012/0255375 A1 | 10/2012 | Kwok et al. | |
| 2012/0302907 A1 | 11/2012 | Palmskog et al. | |
| 2013/0078733 A1 | 3/2013 | Holmes et al. | |
| 2013/0192463 A1 | 8/2013 | Wu et al. | |
| 2013/0319239 A1 | 12/2013 | Takenaka et al. | |
| 2015/0010902 A1 | 1/2015 | Takenaka et al. | |
| 2016/0223435 A1 | 8/2016 | Takenaka et al. | |
| 2016/0249828 A1 | 9/2016 | Blanton et al. | |
| 2017/0059466 A1 | 3/2017 | Park | |
| 2017/0215764 A1 * | 8/2017 | Hamilton ............... | A61B 5/097 |
| 2017/0299477 A1 | 10/2017 | Milton et al. | |
| 2018/0164283 A1 * | 6/2018 | Godula-Jopek .... | B01D 46/0041 |
| 2020/0158603 A1 | 5/2020 | Scialo et al. | |
| 2020/0221973 A1 | 7/2020 | Hojer | |
| 2020/0245899 A1 | 8/2020 | Heanue et al. | |
| 2020/0278275 A1 | 9/2020 | Turgul et al. | |
| 2021/0101437 A1 * | 4/2021 | Birks ................... | G01N 1/2273 |
| 2023/0380720 A1 | 11/2023 | Peumans et al. | |

FOREIGN PATENT DOCUMENTS

| | | |
|---|---|---|
| WO | WO-2018/172760 A1 | 9/2018 |
| WO | WO-2022/079195 A1 | 4/2022 |
| WO | WO-2022/079197 A1 | 4/2022 |

OTHER PUBLICATIONS

Pardon, et al: "Aerosol sampling using an electrostatic precipitator integrated with a microfluidic interface", Sensors and Actuators B: Chemical, vol. 212, pp. 1-16, 2015.
Marple, et al: "Impactor Design", Atmospheric Environment, vol. 10, No. 10, pp. 891-896, 1976.
International Search Report & Written Opinion for Application No. PCT/EP2022/060428 mailed Sep. 29, 2022.

* cited by examiner

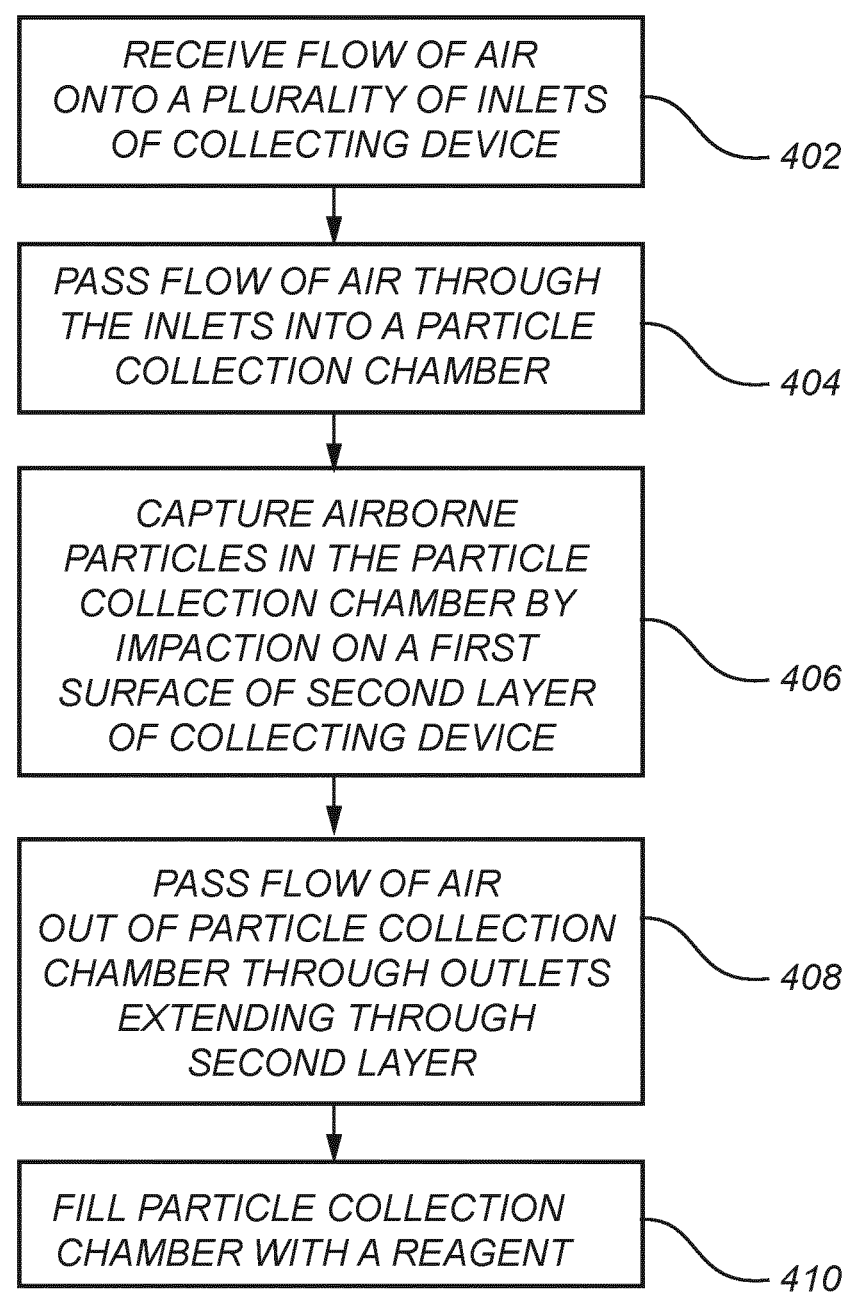

RECEIVE FLOW OF AIR
ONTO A PLURALITY OF INLETS
OF COLLECTING DEVICE ⎯ 402

PASS FLOW OF AIR THROUGH
THE INLETS INTO A PARTICLE
COLLECTION CHAMBER ⎯ 404

CAPTURE AIRBORNE
PARTICLES IN THE PARTICLE
COLLECTION CHAMBER BY
IMPACTION ON A FIRST
SURFACE OF SECOND LAYER
OF COLLECTING DEVICE ⎯ 406

PASS FLOW OF AIR
OUT OF PARTICLE COLLECTION
CHAMBER THROUGH OUTLETS
EXTENDING THROUGH
SECOND LAYER ⎯ 408

FILL PARTICLE COLLECTION
CHAMBER WITH A REAGENT ⎯ 410

Fig. 5

COLLECTING DEVICE AND A METHOD FOR COLLECTION OF AIRBORNE PARTICLES EXHALED BY A HUMAN BEING

TECHNICAL FIELD

The present inventive concept relates to a collecting device and a method for collection of airborne particles exhaled by a human being. In addition, the present inventive concept relates to collection of airborne particles and providing a reagent to the collected particles.

BACKGROUND

Efficient collection of airborne particles exhaled by a human to facilitate analysis is of high interest in various applications. For instance, enabling detection of particular substances in a human breath may provide the possibility of screening for infectious diseases, such as influenza and severe acute respiratory syndrome coronavirus 2 (SARS-CoV-2). Thus, collection of exhaled airborne particles in an efficient and inexpensive way may allow screening to be performed frequently, allow quick identification of persons carrying disease, and consequently reducing spreading of the disease. Several diseases, such as influenza and SARS-CoV-2, spread among humans through droplets and aerosols produced during breathing, blowing, talking, coughing, and sneezing. Thus, it would be of interest to provide a collecting device allowing efficient capture of airborne particles exhaled by a human being and facilitating analysis of substances within the captured particles so as to identify whether the person carries a disease or not.

Further, a sample may need to be prepared before analysis may be performed. For instance, a reagent may need to be added to the collected particles. Thus, in order to facilitate fast and efficient analysis of airborne particles, combining collected particles with a reagent also needs to be performed in an efficient manner.

SUMMARY

An objective of the present inventive concept is to provide a collecting device allowing simple and efficient collection of airborne particles exhaled by a human being. A further objective of the present inventive concept is to allow a reagent to be efficiently provided to the collected particles.

These and other objectives of the present inventive concept are at least partly met by the invention as defined in the independent claims. Preferred embodiments are set out in the dependent claims.

According to a first aspect, there is provided a collecting device for collection of airborne particles exhaled by a human being, said collecting device comprising: a first layer and a second layer, wherein the first layer and the second layer are arranged to be spaced apart for forming a particle collection chamber between the first and the second layer, wherein the first layer comprises a plurality of inlets configured to extend through the first layer for transporting a flow of air therethrough into the particle collection chamber; wherein ends of the inlets are configured to face a first surface of the second layer for capturing airborne particles in the flow of air entering the particle collection chamber through the ends of the inlets by impaction of airborne particles on the first surface of the second layer; wherein the second layer comprises a plurality of outlets configured to extend through the second layer for transporting the flow of air therethrough out of the particle collection chamber; the collecting device further comprising at least one liquid access port for filling the particle collection chamber with a reagent; and wherein the particle collection chamber comprises at least one side wall extending from the first layer to the second layer for defining flow of the reagent through the particle collection chamber when filling the particle collection chamber, such that a first portion of the particle collection chamber and a second portion of the particle collection chamber are arranged on opposite sides of the at least one side wall.

Thanks to the collecting device, an efficient capturing of airborne particles may be provided in the particle collection chamber. The use of a plurality of inlets may ensure that a high capturing efficiency of airborne particles is achieved in the particle collection chamber, as capturing of airborne particles occur in multiple positions of the particle collection chamber (associated with respective inlets).

Further, thanks to the collecting device, capturing of airborne particles may be performed in a particle capturing chamber which may further be filled with a reagent. Thus, the collected particles need not be transferred from the collecting device in which the particles are collected for purpose of providing a reagent. This implies that a very efficient collection and preparation of a sample may be provided by the collecting device.

Further, thanks to the particle collection chamber comprising at least one side wall, flow of the reagent through the particle collection chamber may be controlled. This implies that the flow of the reagent through the particle collection chamber may be well-defined since at least a first portion and a second portion of the particle collection chamber are separated by the at least one side wall. A well-defined flow of the reagent may ensure that bubbles are not trapped within the particle collection chamber after the particle collection chamber has been filled with the reagent. Rather, air (or any other gas) in the particle collection chamber may be pushed in a controlled manner by the reagent towards opening(s) through which the air can escape the particle collection chamber.

The air being pushed out by the filling of the particle collection chamber by the reagent may escape the particle collection chamber through the inlets and/or outlets. However, the collecting device may further comprise a separate outlet port through which the air (or any other gas) in the particle collection chamber may also or alternatively leave the particle collection chamber when it is filled by the reagent.

Ensuring that there are no bubbles in the particle collection chamber may be very advantageous in relation to analysis of the collected particles to be performed. For instance, the analysis of the collected particles may be performed through a light-based measurement, such as by illuminating the collected particles and/or substance(s) extracted from the collected particles and detecting light after interaction with the collected particles. Light interaction may include absorption, transmission, scattering, and fluorescence. If bubbles would be present in the particle collection chamber, the bubbles may interact with light used for analysis, such as illumination light or light having interacted with a sample, such as fluorescent light or scattered light. The bubbles may thus affect analysis based on light-based measurements.

The particle collection chamber is adapted for allowing reactions to take place therein and may also be adapted for allowing measurements to be performed in relation to the collected particles in the particle collection chamber. Thus, analysis of the collected particles may be performed in the particle collection chamber.

Thanks to the collecting device being further configured to allow measurements to be performed while a sample, prepared by the collected particles reacting with the reagent, is arranged in the particle collection chamber, the collecting device facilitates a fast analysis of a sample being made.

Optical access to the particle collection chamber may be provided by the first and/or the second layer being transparent to wavelengths of light being used in the light-based measurement. Additionally or alternatively, optical access may be provided through the inlets and/or the outlets defining a space (which may possibly be filled by a liquid reagent) through which optical access to the particle collection chamber is provided.

The collecting device may facilitate an easy and intuitive way of collecting samples through self-test by persons, thereby promoting more frequent testing of people. In this regard, the use of the collecting device for screening of people may allow people to be screened several times per week, such as every day, such that viral load peaks may be identified. If testing is done only once a week, the viral load peak may be missed such that the testing fails to detect persons having a stage of a disease in which the person is highly infectious. Hence, very frequent testing may be required in order to identify highly infectious people and prevent spreading of a disease.

The reagent may be a liquid reagent. The collecting device is configured to receive the reagent through the at least one liquid access port. The reagent may then flow into the particle collection chamber in order to completely fill the particle collection chamber.

The at least one side wall extending from the first layer to the second layer implies that reagent may not leak between the first layer and the side wall or the second layer and the side wall so as to flow from the first portion to the second portion of the particle collection chamber. Thus, the at least one side wall firmly controls flow of the reagent for filling the particle collection chamber.

Both the first and the second portion of the particle collection chamber need not be in direct contact with the at least one side wall. For instance, the particle collection chamber may comprise two parallel side walls, with a spacing therebetween not being part of the particle collection chamber. This implies that a first side wall may form a wall of the first portion and a second side wall may form a wall of the second portion of the particle collection chamber.

Further, the first and second portions of the particle collection chamber need not be completely sealed from each other. Rather, the first and second portions may be connected to each other at an end of the particle collection chamber, which implies that the reagent will be guided to follow a non-straight path through the particle collection chamber when filling the particle collection chamber.

The at least one side wall may further provide support between the first and second layers of the collecting device. This implies that a structural stability of the collecting device is improved by the at least one side wall. Further, the at least one side wall may improve bonding of the first and second layers to each other in manufacturing of the collecting device.

As used herein, capturing of airborne particles by "impaction" should be construed as particles being removed from the flow of air by forcing the flow of air to change direction. Thanks to the flow of air being forced to change direction, momentum of particles having a certain size will cause the particles not to follow the flow of air in its change of direction and instead the particles will be captured on a collection surface. The capturing of airborne particles may involve capturing of aerosols but may also or alternatively involve capturing of larger droplets in the flow of air.

According to an embodiment, the airborne particles may be borne e.g. by aerosols and/or by droplets in the air exhaled by a person. The airborne particles may further comprise substance(s) of interest, such that analysis of the collected particles may include the particles being subject to reactions for exposing the substance(s) of interest to enable detection of substance(s) of interest in a measurement.

Further, thanks to the collecting device comprising a plurality of inlets and a plurality of outlets, the collecting device facilitates breathing through the collecting device without requiring a high supply pressure to be provided by the person breathing through the collecting device. In particular, the use of a plurality of inlets and outlets enables the flow of air to experience a combined cross-section of the respective inlets and outlets that is relatively large such that a large pressure drop may be avoided even though individual inlets and outlets may have small cross-sections. Further, the small cross-sections facilitate particle collection at low flow rates of the flow of air, such as in the order of 0.5 liters per second.

The collecting device allows a human being to breath or blow into the collecting device such that particles comprised in the exhaled air can be conveniently collected without requiring difficult procedures for the person. Compared to sample collection through a nasal or throat swab, or saliva collection, the collecting device provides a particle collection with much less discomfort for the user and may remove the need for a trained professional to be involved in the sample collection.

The flow of air may be received by the collecting device by the human being blowing directly into an apparatus holding the collecting device, such as through a mouthpiece of the apparatus. Hence, the flow of air may be provided directly from exhalation by the human being. However, it should be realized that the flow of air may alternatively be received indirectly from the human being, e.g. by the human being exhaling into a bag and by the flow of air being provided by the bag towards the collecting device.

The first layer and the second layer may be parallel and define planar surfaces on opposite sides of the particle collection chamber. It should further be realized that the particle collection chamber may further be defined by outermost side walls surrounding an outer periphery of the particle collection chamber. The outermost side walls (together with the at least one side wall) may also provide a spacer for defining a distance between the first layer and the second layer.

The inlets and the outlets may extend from the particle collection chamber to an external environment outside the collecting device. Thus, the inlets may extend through at least the first layer and possibly further layers between the particle collection chamber and the external environment. Similarly, the outlets may extend through at least the second layer and possibly further layers between the particle collection chamber and the external environment.

The inlets may further be defined by walls extending from the first layer into the particle collection chamber and towards the second layer. Thus, the ends of the inlets facing the first surface of the second layer need not be flush with the first layer. Rather, the ends of the inlets may arranged close to the second layer, which may facilitate capturing of particles, while the distance between the first and second layers may be larger than the distance between the ends of the inlets and the second layer to allow a larger volume of the particle collection chamber.

At least the first and second layers of the collecting device may be formed from a semiconductor or semiconductor-based material, such as silicon or silicon dioxide. This may facilitate manufacturing of the collecting device, since small dimensions of the collecting device may be advantageously provided by semiconductor manufacturing processes.

According to an embodiment, the particle collection chamber extends in an area of a plane parallel to the first layer and wherein the at least one liquid access port is arranged at or close to a periphery of the area.

This implies that the reagent may enter the particle collection chamber through a periphery of the area or close to the periphery of the area. Then, the particle collection chamber will be filled from a point of entry into the particle collection chamber. This may ensure that the reagent need not flow in all directions for filling the particle collection chamber (as opposed to if the reagent is entered into the particle collection chamber at a central position of the area). Hence, a risk for bubbles being trapped in the particle collection chamber is further reduced.

The at least one liquid access port may be arranged inside the periphery of the area or outside the periphery of the area. Even if the liquid access port is inside the periphery of the area, since the access port is close to the periphery, a risk of bubbles being trapped in the particle collection chamber may be low.

The liquid access port may be directly connected to the particle collection chamber or may be connected to the particle collection chamber via a connecting channel. Thus, the reagent may be received at the at least one liquid access port and may then be guided through the connecting channel before entering the particle collection chamber at the periphery of the area. In fact, in embodiments with a connecting channel connecting the liquid access port to a periphery of the area, the liquid access port may be distanced from the periphery of the area by a long connecting channel.

The liquid access port being connected to the particle collection chamber through a connecting channel implies that the liquid access port may be spaced apart from inlets (or outlets) even though the liquid access port extends through the first layer (or second layer). This implies that a space around the particle collection chamber in which particles carrying an infectious disease may be sealed as soon as the particles have been collected and, yet, the reagent may be provided into the particle collection chamber. Thus, a further sealing of the connecting channel and the liquid access port may be performed when the reagent has been provided.

According to an embodiment, the plurality of inlets and the plurality of outlets are distributed over the area of the particle collection chamber.

The inlets and outlets may function to allow air to escape the particle collection chamber when the particle collection chamber is filled by the reagent. Thanks to the inlets and outlets being distributed over the area, outlet of air is provided in the entire area of the particle collection chamber. This may further ensure that no bubbles are trapped in the particle collection chamber when it is filled by the reagent.

The plurality of inlets and the plurality of outlets may be evenly distributed over the area such that the plurality of inlets and the plurality of outlets are arranged in a regular pattern over an entire area of the particle collection chamber.

This may imply that distances between adjacent inlets and between adjacent outlets is equal over the entire area of the particle collection chamber.

By having a plurality of inlets arranged with small distances between adjacent inlets and arranged to be distributed over the area of the particle collection chamber, a large collection efficiency of the collecting device may be provided using a small footprint of the collecting device.

According to an embodiment, the particle collection chamber is configured for guiding propagation of the reagent from the at least one liquid access port through the particle collection chamber along the at least one side wall, wherein the reagent is guided through a channel having a larger length in a main direction of propagation of the reagent than width transverse to the main direction.

The channel having a larger length than width implies that the reagent may easily fill the width transverse to the main direction as the reagent flows along the length of the channel. This implies that there is a low risk for bubbles being trapped within the particle collection chamber at sides of the channel.

It should be realized that, when referring to the width of the channel, it is referred to a size of the channel in a transverse direction to the main direction in the plane of the particle collection chamber parallel to the first layer.

It should be further realized that the length of the channel may be defined as a path length of a center line of the channel, which may or may not follow a straight path.

According to an embodiment, the particle collection chamber is separated by the at least one side wall into a plurality of separate compartments, such that the first portion and the second portion form a first compartment and a second compartment, respectively.

Thanks to the particle collection chamber having separate compartments, the separate compartments may be separately and simultaneously filled. This implies that an efficient and fast filling of the particle collection chamber with a reagent may be provided with a relatively large total volume of the particle collection chamber. This also implies that an analysis result may be quickly provided through sampling by the collecting device.

The first and second compartments may each receive flow of air from a plurality of inlets configured to extend through the first layer. Thus, the flow of air from exhalation by the human being may be incident on a surface of the first layer so as to simultaneously provide the flow of air through respective inlets to the first and second compartments. This implies that the collection of particles may be easily provided simultaneously in a plurality of compartments of the particle collection chamber.

Each inlet may be associated with a single compartment, such that each compartment may be associated with a set of inlets dedicated to the compartment.

It should be realized that the particle collection chamber may be separated into more than two compartments, such as three, eight or sixteen compartments, or any other suitable number.

According to an embodiment, the collecting device comprises a plurality of liquid access ports, each liquid access port being associated with a unique compartment of the particle collection chamber.

Thus, the compartments of the particle collection chamber may each be supplied through a dedicated liquid access port. This may ensure that reagent is supplied in a well-controlled manner to each compartment for filling all the compartments of the particle collection chamber simultaneously. Also, each of the compartments is individually controlled, such that the compartments may be filled in different manners, if desired, such as by providing different reagents to different compartments.

According to another embodiment, the collecting device comprises a single liquid access port for filling each of the plurality of compartments of the particle collection chamber.

Thus, reagent may be supplied to all of the plurality of compartments through a single liquid access port. Hence, filling of all of the compartments may be performed in a simple manner. The liquid access port may be branched into separate channels, each being connected to a unique compartment.

According to an embodiment, the at least one side wall is configured to define a non-straight path of propagation of the reagent from the at least one liquid access port through the particle collection chamber.

Thus, flow of reagent when filling the particle collection chamber may follow a narrow channel, while the particle collection chamber may have a small footprint in two dimensions of the plane of the particle collection chamber, such as providing a square shape of the outer periphery of the particle collection chamber.

The non-straight path may include both the first portion of the particle collection chamber and the second portion of the particle collection chamber. This may also imply that there is a fluid connection between all parts of the particle collection chamber.

According to an embodiment, the non-straight path is meander-shaped.

This is an efficient manner of arranging the channel along the non-straight path formed by the particle collection chamber in a small area of the outer periphery of the particle collection chamber.

According to an embodiment, the at least one liquid access port has cross-sectional dimensions for allowing the reagent to be passed through the at least one liquid access port into the particle collection chamber by a capillary force.

This implies that reagent may be supplied into the particle collection chamber in a simple manner. The capillary force may draw reagent into the particle collection chamber. Hence, the reagent may simply be provided as droplet(s) on a surface at which the at least one liquid access port provides an opening.

According to an embodiment, the at least one liquid access port is configured to extend through the first layer or the second layer.

Thus, the at least one liquid access port may provide access to the particle collection chamber at a surface of the collecting device which may also provide access to the particle collection chamber via inlets or outlets.

According to an embodiment, the inlets and the outlets have dimensions for allowing the inlets and the outlets to be filled by the reagent from the particle collection chamber by a capillary force, wherein the capillary force further prevents the reagent to escape from the inlets and the outlets.

Thus, the particle collection chamber and the inlets and outlets connected thereto in the collecting will be completely filled by the reagent. This may ensure that any air within a space in the collecting device connected to the particle collection chamber is pushed out of the collecting device when the particle collection chamber is filled by the reagent. Hence, a risk for bubbles being trapped in the particle collection chamber is further reduced.

This may further facilitate high quality light-based measurements of a sample in the particle collection chamber. in particular if optical access is provided through the inlets and/or outlets. By the inlets and outlets being filled with reagent, light will not need to pass and will hence not be affected by an interface between air and the reagent at an entry of the inlet or outlet into the particle collection chamber. Further, an interface between air and reagent may be avoided at an interface to an external environment outside the collecting device, by a layer being placed in contact with the collecting device. Such layer may also function to seal the particle collection chamber.

According to an embodiment, the collecting device further comprises pillars extending from the first layer to the second layer for improving bonding of the first layer to the second layer.

The pillars may provide support between the first and second layers of the collecting device. This implies that a structural stability of the collecting device is improved by the pillars. Further, the pillars may improve bonding of the first and second layers to each other in manufacturing of the collecting device.

According to a second aspect, there is provided a method for collection of airborne particles exhaled by a human being and providing a reagent to the collected particles, said method comprising: receiving a flow of air onto a first layer of a collecting device, wherein the first layer comprises a plurality of inlets extending through the first layer; passing the flow of air through the inlets into a particle collection chamber between the first layer and a second layer of the collecting device spaced apart from the first layer; capturing airborne particles in the flow of air entering the particle collection chamber by impaction of airborne particles on a first surface of the second layer, wherein ends of the inlets are configured to face the first surface of the second layer; passing the flow of air out of the particle collection chamber through outlets extending through the second layer of the collecting device; filling the particle collection chamber with a reagent through at least one liquid access port, wherein the reagent is guided to flow through the particle collection chamber along at least one side wall through a first portion of the particle collection chamber and a second portion of the particle collection chamber on opposite sides of the at least one side wall.

Effects and features of this second aspect are largely analogous to those described above in connection with the first aspect. Embodiments mentioned in relation to the first aspect are largely compatible with the second aspect.

Thanks to the method, an efficient capturing of airborne particles may be provided in the particle collection chamber. Further, thanks to the method, capturing of airborne particles is performed in a particle capturing chamber which is further filled with a reagent. Thus, the collected particles need not be transferred from the collecting device in which the particles are collected for purpose of providing a reagent. This implies that a very efficient collection and preparation of a sample may be provided by the collecting device.

Further, thanks to the reagent being guided to flow along at least one side wall through first and second portions of the particle collection chamber on opposite sides of the at least one side wall, flow of the reagent through the particle collection chamber is controlled. This implies that the flow of the reagent through the particle collection chamber may be well-defined since at least a first portion and a second portion of the particle collection chamber are separated by the at least one side wall. The well-defined flow of the reagent may ensure that bubbles are not trapped within the particle collection chamber after the particle collection chamber has been filled with the reagent.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 5 is a flowchart of a method according to an embodiment.

DETAILED DESCRIPTION

Figure 1:
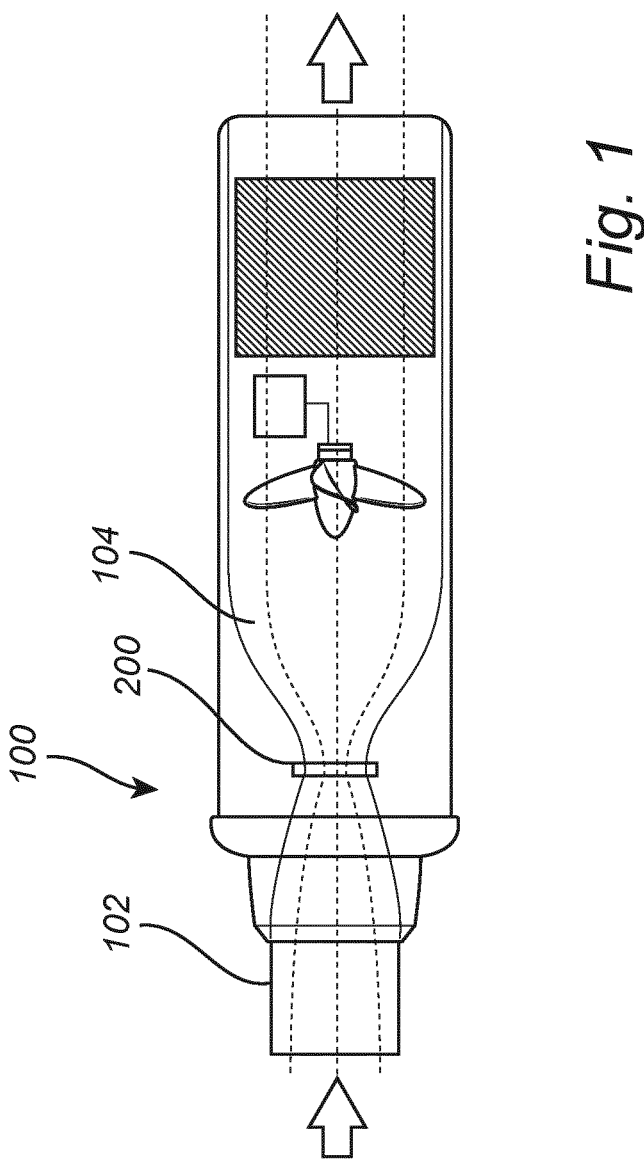
FIG. 1 is a schematic cross-sectional view of a sample collector including a collecting device for collection of airborne particles according to an embodiment.

Referring now to FIG. 1, a collecting device 200 for collection of airborne particles exhaled by a human being is shown in relation to a sample collector 100. It should thus be realized that according to an embodiment, the collecting device 200 may be arranged in a sample collector 100 which provides an interface for allowing a flow of air from a human being to be provided through the collecting device 200. However, it should be realized that the collecting device 200 may be arranged to receive the flow of air in different manners and need not necessarily be mounted in a sample collector 100 or any other apparatus.

The sample collector 100 may be used for capturing airborne particles, such as aerosols and/or droplets in the flow of air exhaled by the human being. Thanks to capturing airborne particles, analysis of the airborne particles in the exhaled breath may be performed. This may be used for determining whether the human being carries a disease, which is spread through droplets and aerosols produced during normal breathing, talking, coughing, and sneezing. For instance, the capturing of airborne particles using the sample collector 100 may be used for screening whether a person is infected by influenza or severe acute respiratory syndrome coronavirus 2 (SARS-CoV-2). Thanks to the sample collector 100 capturing a sample based on an exhaled breath, the capturing of a sample from a person may be performed with minimal discomfort to the person.

The sample collector 100 may comprise a mouthpiece 102 to be inserted into the mouth of the person and through which the person exhales to provide a flow of air 104 through the sample collector 100.

The flow of air 104 may be guided through the sample collector 100 so as to pass the collecting device 200. The collecting device 200 is configured to capture airborne particles from the flow of air 104 through impaction in a particle collection chamber of the collecting device 200. The collecting device 200 may be configured to capture airborne particles with high efficiency and may further allow analysis of the collected airborne particles.

Analysis of the collected airborne particles involves sample preparation by providing a reagent to the particle collection chamber for allowing reactions to take place in the particle collection chamber. The sample collector 100 may be configured to provide access to the collecting device 200 arranged in the sample collector 100 such that a reagent may be provided to the particle collection chamber while the collecting device 200 is arranged in the sample collector 100.

The reactions may further be controlled by providing further influence on the particle collection chamber, such as by heating and/or cooling the sample in the particle collection chamber.

Furthermore, analysis of the collected airborne particles may be performed while the collecting device 200 is maintained in the sample collector 100. This implies that a risk of spreading of disease by opening of the sample collector 100 may be avoided.

Figure 2:
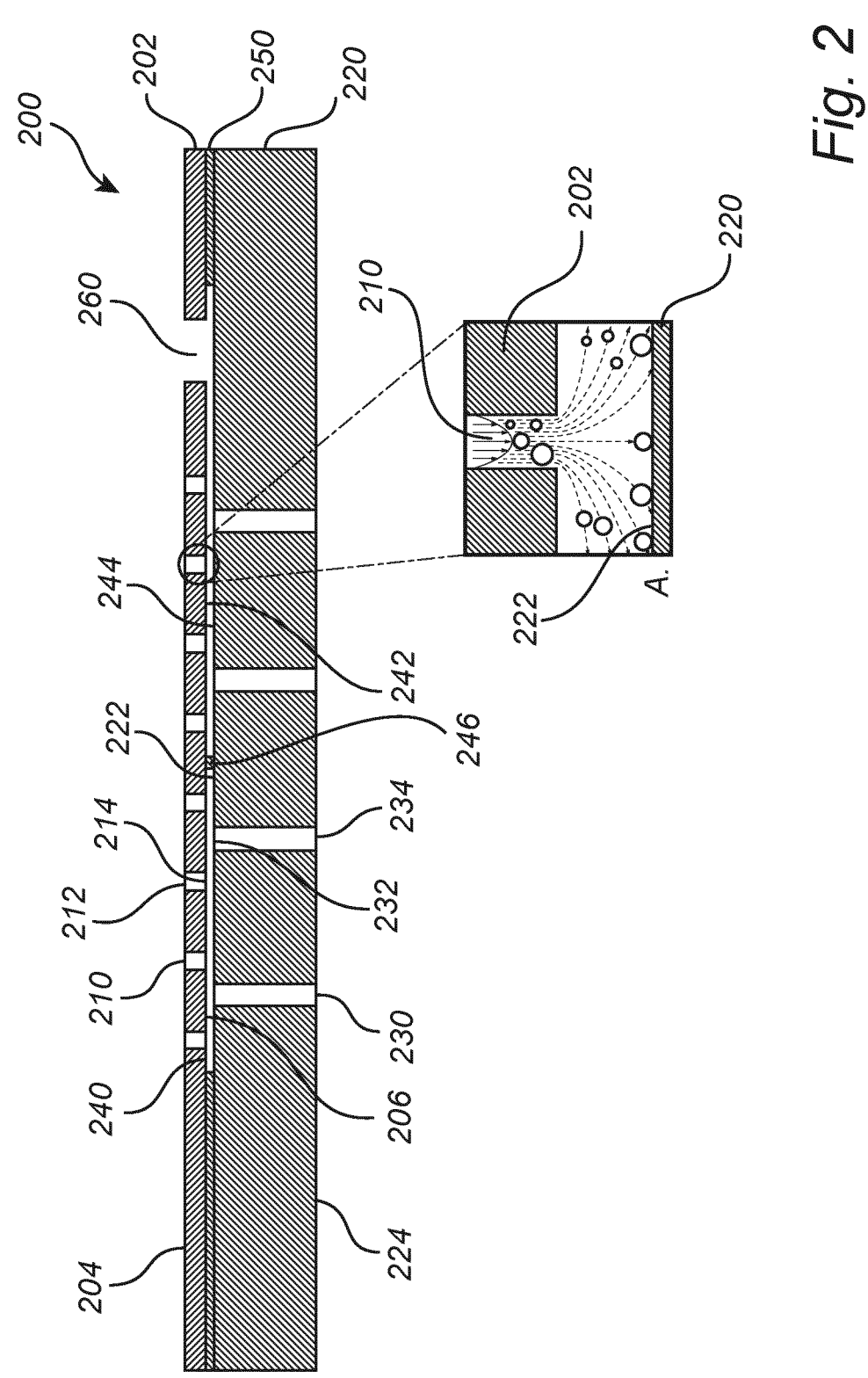
FIG. 2 is a schematic cross-sectional view of a collecting device according to an embodiment.

Referring now to FIG. 2, the collecting device 200 according to an embodiment will be further described.

The collecting device 200 comprises a first layer 202 and a second layer 220. The first layer 202 and the second layer 220 are arranged to be spaced apart for defining a particle collection chamber 240 between the first layer 202 and the second layer 220.

The first layer 202 and the second layer 220 may each be formed from a semiconductor or semiconductor-based material, such as silicon or silicon dioxide. This may facilitate manufacturing of the collecting device 200, since small dimensions of the collecting device may be advantageously provided by semiconductor manufacturing processes.

The first layer 202 comprises a first surface 204 configured to receive a flow of air, which may be the flow of air 104 in the sample collector 100 as described above. The first layer 202 also comprises a second surface 206 facing the second layer 220. The first layer 202 further comprises a plurality of inlets 210 having a first end 212 at the first surface 204 of the first layer 202 and a second end 214 at the second surface 206 of the first layer 204.

The second layer 220 comprises a first surface 222 facing the first layer 202 and a second surface 224 at which the flow of air may be output from the collecting device 200 after having passed the collecting device 200. The second layer 220 further comprises a plurality of outlets 230 having a first end 232 at the first surface 222 of the second layer 220 and a second end 234 at the second surface 224 of the second layer 220.

The inlets 210 are configured to extend through the first layer 202 for transporting the flow of air 104 through the first layer 202 from the first end 212 to the second end 214. The second ends 214 of the inlets 210 are configured to face the first surface 222 of the second layer 220. Thus, when the flow of air 104 passes through the inlets 210, the flow of air 104 will impinge on the first surface 222 of the second layer 220 such that airborne particles may be collected on the first surface 222 of the second layer 220 and, hence, in the particle collection chamber 240, by impaction.

The particle collection chamber 240 has first side 242 and a second side 244, wherein the first side 242 is defined by the second surface 206 of the first layer 204 and the second side 244 is defined by the first surface 222 of the second layer 220. The particle collection chamber 240 may further be defined by side surfaces formed in a spacer material 250 between the first layer 202 and the second layer 220.

The spacer 250 can either be a glue, double sided-adhesive tape, or in case of silicon/glass layers 202, 220, the spacer 250 can be integrated into one of the layer materials to enable anodic, fusion, or laser bonding of the first layer 202 and the second layer 220.

In another embodiment, not shown in FIG. 2, the inlets 210 may be configured to protrude from second surface 206 of the first layer 202 to extend further into the particle collection chamber 240. This may imply that the second ends 214 of the inlets 210 are closer to the first surface 222 of the second layer 220 so as to improve capturing of particles by impaction while ensuring that a volume of the particle collection chamber 240 is not too small.

The inlets 210 and the outlets 230 are arranged in a staggered arrangement. This implies that center axes of inlets 210 and outlets 230 are not aligned. Hence, the flow of air 104 passing through the inlets 210 into the particle collection chamber 240 will at least slightly change direction through the particle collection chamber 240 before the flow of air 104 may exit the particle collection chamber 240 through the outlets 230.

Thanks to the inlets 210 and the outlets 230 being staggered, the inlets 210 are arranged directly above the first surface 222 of the second layer 220 wherein capturing of airborne particles occur. The inlets 210 are arranged such that there is at least no opening in the first surface 222 of the second layer 220 corresponding to an outlet 230 at a projection of the center axes of the inlets 210 onto the first surface 222 of the second layer 220. As shown in FIG. 2, the inlets 210 and the outlets 230 are arranged such that the entire inlet 210 is projected on an area of the first surface 222 wherein no openings corresponding to outlets 240 are provided. Thus, airborne particles may be captured at the first surface 222 of the second layer 220, while the flow of air 104 through the inlets 210 changes direction to follow the first surface 222 and then escape the particle collection chamber 240 through the outlets 230.

As shown in FIG. 2, the inlets 210 may extend perpendicularly in relation to the first layer 202. Further, the outlets 230 may extend perpendicularly in relation to the second layer 220. With the first and second layer 202, 220 being parallel, this implies that the inlets 210 and the outlets 230 are parallel, arranged with the central axes displaced in relation to each other. This is a suitable arrangement for ensuring that the inlets 210 and outlets 230 are staggered and that the flow of air 104 is forced to change direction through the collecting device 200.

Thanks to the flow of air 104 being forced to change direction, momentum of airborne particles having a certain size will cause the airborne particles not to follow the flow of air 104 in its change of direction and instead the particles will be captured on the collection surface formed by the first surface 222 of the second layer 220. The capturing of airborne particles may involve capturing of aerosols but may also or alternatively involve capturing of larger droplets in the flow of air.

Collection of particles in the collecting device 200 is further illustrated in the enlarged insert A of FIG. 2, illustrating that airborne particles will be captured by impaction on the first surface 222 of the second layer 220, before the flow of air 104 proceeds to outlets 230 extending through the second layer 220.

The collecting device 200 may further be configured to provide optical access for performing a measurement, based on light, of airborne particles collected in the particle collection chamber 240.

The measurement may be performed based on light that is passed through at least one of the first and second layers 202, 220. Thus, the first layer 202 and/or the second layer 220 may be transparent or translucent to provide optical access to the particle collection chamber 240. However, according to another embodiment, optical access is provided through the inlets 210 and/or the outlets 230.

In addition to the inlets 210 and outlets 230, a liquid access port 260 providing a reagent inlet is provided in the collecting device 200. The liquid access port 260 may extend through the first layer 202 as shown in FIG. 2 but may alternatively extend through the second layer 220 instead. The liquid access port 260 enables filling of the particle collection chamber 240 with a liquid reagent, such as a polymerase chain reaction (PCR) reagent. The filling of the particle collection chamber 240 by the reagent will be discussed in further detail below.

The collecting device 200 may further be configured to allow a sample in the particle collection chamber 240 to be heated and/or cooled, possibly in numerous iterations, in order to prepare the sample for analysis. For instance, thermal energy may be provided to the particle collection chamber 240 for thermal lysis to expose RNA of SARS-CoV-2 in the captured particles, converting the RNA to DNA using reverse transcriptase based on the reagent and providing thermal cycling for amplification of the DNA using quantitative PCR.

As mentioned above, analysis of a sample in the particle collection chamber 240 may be performed by light-based measurements of the sample. The reagent should therefore be filled into the particle collection chamber 240 such that bubbles are not trapped in the particle collection chamber 240, since bubbles may affect light-based measurement results.

Figure 3:
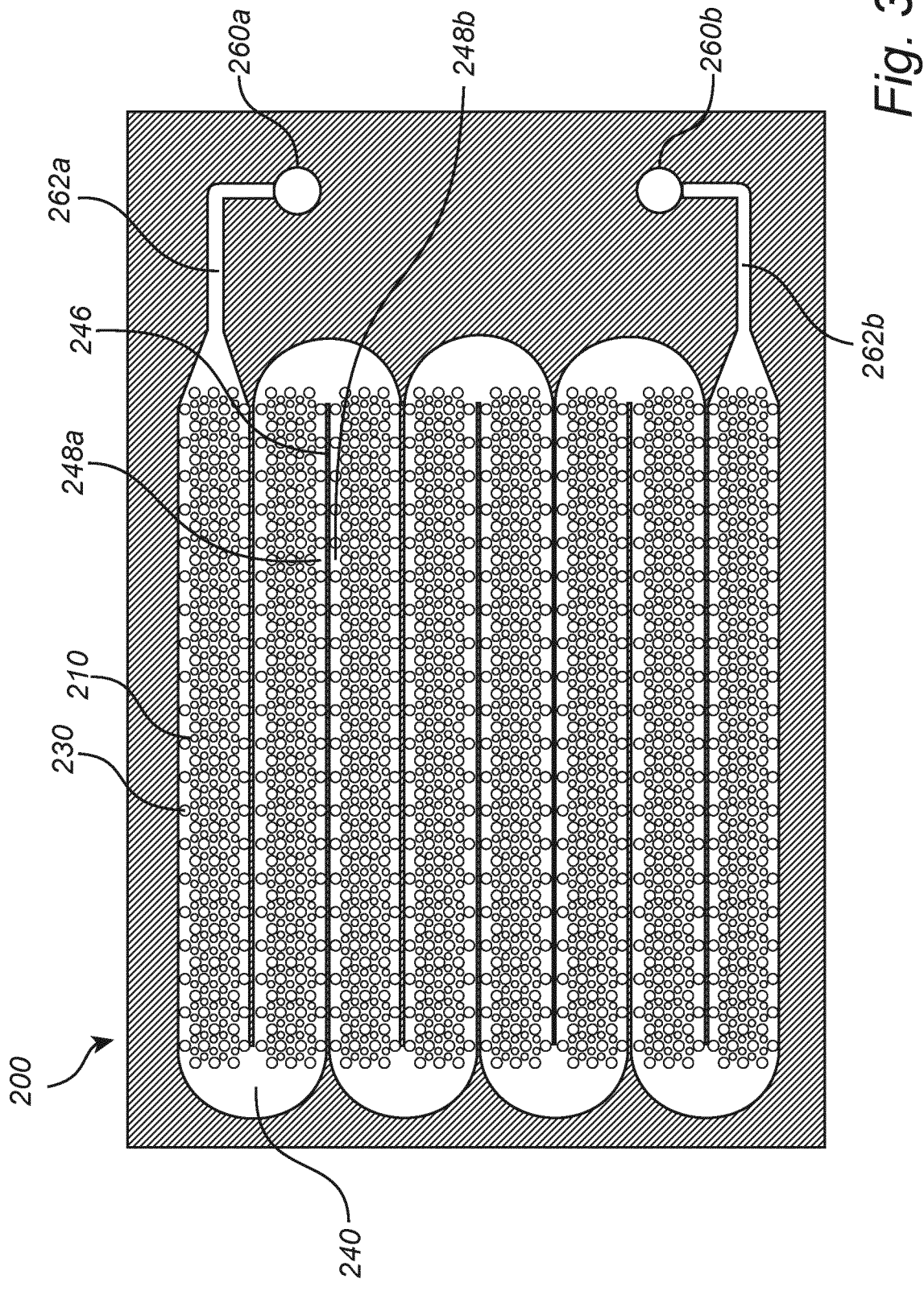
FIGS. 3-4 are schematic views illustrating arrangement of inlets, outlets, a particle collection chamber, and liquid access ports of the collecting device according to different embodiments.

Referring now to FIG. 3, a particle collection chamber 240 according to a first embodiment is shown. The particle collection chamber 240 is formed such that trapping of bubbles in the particle collection chamber 240 during filling of the particle collection chamber 240 with a liquid reagent may be reduced or avoided.

FIG. 3 shows a top view of the particle collection chamber 240 with the first layer 202 and the second layer 220 being removed from the view, whereas the inlets 210 and the outlets 230 are illustrated to indicate the relations between the inlets 210 and the outlets 230 and the particle collection chamber 240. However, lateral walls surrounding the particle collection chamber 240 are indicated in FIG. 3.

The particle collection chamber 240 comprises at least one side wall 246 within an area defined by an outer periphery of the particle collection chamber 240. The area of the particle collection chamber 240 extends in a plane parallel to the first layer 202 and the second layer 220. Thus, the at least one side wall 246 provides guidance of flow of the reagent when the particle collection chamber 240 is filled. As shown in FIG. 3, a plurality of side walls 246 may be provided such that the plurality of side walls 246 cooperate to provide guidance of the flow of the reagent. For brevity and simplicity, description below will mainly be made in relation to one of the side walls 246, but it should be realized that the description may apply to each of the plurality of side walls 246.

Since the particle collection chamber 240 comprises the side wall 246, the particle collection chamber 240 also comprises a first portion 248a and a second portion 248b arranged on opposite sides of the side wall 246. The side wall 246 extends from the first layer 202 to the second layer 220 implies that reagent may not leak between the first layer 202 and the side wall 246 or the second layer 220 and the side wall 246 so as to flow directly from the first portion 248a to the second portion 248b of the particle collection chamber 240.

Thanks to the side wall 246 the flow of the reagent may be guided along a path through the particle collection chamber 240. In particular, the flow of the reagent may be guided to flow along the side wall 246 such that the flow of the reagent propagates within a relatively narrow angle in relation to a main direction of the flow. This implies that the reagent may push air (or any other gas) in the particle collection chamber 240 in front of a wavefront of the flow of reagent towards opening(s) of the particle collection chamber 240 through which the air (or other gas) can escape. Hence, the arrangement of the particle collection chamber 240 may ensure that bubbles are not trapped within the particle collection chamber 240 when the particle collection chamber 240 is filled by the reagent.

The openings through which air may escape the particle collection chamber 240 may be formed by the inlets 210 and/or outlets 230. However, the collecting device 200 may further comprise a separate outlet port through which the air (or other gas) in the particle collection chamber 240 may also or alternatively escape the particle collection chamber 240 when it is filled by the reagent.

The collecting device 200 shown in FIG. 3 comprises two liquid access ports 260a, 260b. The liquid reagent may be supplied to each of the liquid access ports 260a, 260b. For instance, liquid reagent may be simultaneously supplied to the liquid access ports 260a, 260b. Use of two liquid access ports 260a, 260b enables the particle collection chamber 240 to be filled from two ends of the particle collection chamber 240 such that the reagent flowing from each end may meet at a center of the particle collection chamber 240. This implies that the filling of the particle collection chamber 240 may occur from two directions simultaneously such that a time required for filling the particle collection chamber 240 may be reduced by a factor $\sqrt{2}$ compared to a collecting device 200 having only a single liquid access port 260.

Each of the liquid access ports 260a, 260b may be arranged at or close to the outer periphery of the particle collection chamber 240. Since the liquid reagent may thus enter the particle collection chamber 240 close to the periphery of the particle collection chamber 240, the liquid reagent is limited by the periphery of the particle collection chamber 240 from propagating in any direction from the point of entry. Thus, flow of the reagent when filling the particle collection chamber 240 can be further controlled and a risk for bubbles being trapped in the particle collection chamber 240 is further reduced.

As shown in FIG. 2, the liquid access port 260 may provide an opening at a top or bottom surface of the collecting device 200, which surface may be defined by the first layer 202 or the second layer 220 or another layer parallel thereto (if there are plural layers between the top/bottom surface of the collecting device 200 and the particle collection chamber 240). The liquid access port 260 may extend into the particle collection chamber 240, thus extending through either the first layer 202 or the second layer 220, such that the reagent is entered into the particle collection chamber 240 through the first side 242 or the second side 244.

However, as shown in FIG. 3, the liquid access ports 260a, 260b may alternatively end outside the outer periphery of the particle collection chamber 240 in the plane of the particle collection chamber 240. The collecting device 200 further comprises short connecting channels 262a, 262b connecting each of the liquid access ports 260a, 260b into the particle collection chamber 240 at the periphery of the particle collection chamber 240. Thus, the short connecting channels 262a, 262b may transport the reagent from the respective liquid access ports 262a, 262b to the particle collection chamber 240.

Thanks to the liquid ports 260a, 260b being at least slightly spaced from the outer periphery of the particle collection chamber 240, the particle collection chamber 240 with the inlets 210 and outlets 230 may be sealed as soon as the particles (which may carry an infectious disease) have been collected. Still, the reagent may be provided into the particle collection chamber 240 through the liquid access ports 260a, 260b and the connecting channels 262a, 262b and a further sealing of the connecting channels 262a, 262b and the liquid access ports 260a, 260b may be performed when the reagent has been provided.

As mentioned, the liquid access ports 260a, 260b may be configured to extend through the first layer 202 or the second layer 220. The liquid access ports 260a, 260b may be arranged on the same side of the collecting device 200 such that the liquid access ports 260a, 260b extend through the same layer, e.g. the first layer 202. However, according to an alternative, the liquid access ports 260a, 260b may be arranged on opposite sides of the collecting device 200 such that one liquid access port (e.g., liquid access port 260a) extends through the first layer 202 and the other liquid access port (e.g., liquid access port 260b) extends through the second layer 220.

The liquid access ports 260a, 260b may be configured to draw reagent into the liquid access ports 260a, 260b by a capillary force. Thus, the liquid access ports 260a, 260b may have a cross-sectional size, such as a cross-sectional diameter that is sufficiently small for the reagent to be drawn into the particle collection chamber 240. This may typically be achieved by the liquid access ports 260a, 260b having a diameter of an order of millimeters or less.

The collecting device 200 comprises a plurality of inlets 210 and a plurality of outlets 230 for providing the flow of air 104 through the collecting device 200 for capturing airborne particles. The inlets 210 and outlets 230 may further function as openings of the particle collection chamber 240 through which air in the particle collection chamber 240 may escape when the particle collection chamber 240 is filled by the reagent.

The plurality of inlets 210 and the plurality of outlets 230 may be distributed over the area of the particle collection chamber 240. This implies that capturing of particles may occur distributed over the entire area of the particle collection chamber 240, such that a high efficiency of particle collection may be achieved. Further, thanks to the inlets 210 and outlets 230 being distributed over the area of the particle collection chamber 240, the particle collection chamber 240 is provided with openings allowing air to escape from the particle collection chamber 240 throughout the area of the particle collection chamber 240. Thus, a risk for bubbles being trapped in the particle collection chamber 240 is further reduced.

The inlets 210 and the outlets 230 may be configured to draw reagent from the particle collection chamber 240 into the inlets 210 and outlets 230 by a capillary force. Thus, the inlets 210 and the outlets 230 may have a cross-sectional size, such as a cross-sectional diameter that is sufficiently small for the reagent to be drawn into the inlets 210 and the outlets 230. The inlets 210 and the outlets 230 may anyway desirably have a small cross-sectional dimension to allow efficient capturing of particles of a small size, such that the inlets 210 and the outlets 230 may anyway be so small as to provide a capillary force for drawing the reagent into the inlets 210 and the outlets 230. For instance, the inlets 210 may have a diameter in a range of 20-300 μm, such as in a range of 100-200 μm for providing efficient collection of particles down to a size of 300 nm. Further, the outlets 230 may be dimensioned in relation to the inlets 210. For instance, the outlets 230 may have a diameter in the range of 20-400 μm, such as in the range of 100-300 μm.

Thanks to the small cross-sectional sizes of the inlets 210 and the outlets 230, the capillary force may also prevent the reagent from escaping from the inlets 210 and the outlets

230 at an interface to a top or bottom surface of the collecting device 200, respectively. Since the inlets 210 and the outlets 230 may open to a large surface of the collecting device 200, the capillary force will keep the reagent inside the inlets 210 and the outlets 230, respectively.

As shown in FIG. 3, the side walls 246 define a channel through the particle collection chamber 240 for guiding the flow of reagent when the particle collection chamber 240 is filled from the entry of the reagent into the particle collection chamber 240. The flow of reagent may enter the particle collection chamber 240 through a connecting channel 262a, 262b such that the flow of reagent propagates along a main direction defined by the connecting channel 262a, 262b when entering the particle collection chamber 240. The channel of the particle collection chamber 240 may further guide the flow of reagent along the main direction along the side walls 246. The channel in the particle collection chamber 240 preferably has a larger length in the main direction of propagation of the reagent than width transverse to the main direction. This implies that the reagent may easily fill the width transverse to the main direction as the reagent flows along the length of the channel. This implies that there is a low risk for bubbles being trapped within the particle collection chamber 240 at sides of the channel.

As further shown in FIG. 3, the side walls 246 define a non-straight path through the particle collection chamber 240. In particular, the side walls 246 define a meander-shaped path through the particle collection chamber 240. Thus, flow of reagent when filling the particle collection chamber 240 follows a narrow channel, while the particle collection chamber 240 has a small footprint in two dimensions of the plane of the particle collection chamber 240.

The use of a narrow channel having a long length as shown in FIG. 3 implies that the time required for filling the particle collection chamber 240 by the reagent may be relatively long. This implies that the reagent filling time may account for a large proportion of the time required for performing an analysis using the collecting device 200.

In some applications, the time required for performing an analysis may be of importance. For instance, with a test that may be quickly performed, such as within 5 minutes or 15 minutes from airborne particles being captured, a high throughput of test results may be provided. This implies that tests may be suitable to be performed at a point that is passed by many people for screening people at such a point. For instance, tests may suitably be made at an entrance to an airport, a shop, or a company facility, for screening people for infectious diseases, such as SARS-CoV-2 before admitting people through the entrance. The high throughput of testing may allow such screening to be performed without long queues being formed. Hence, it may be desired that the reagent filling time is very short, such as shorter than 10 s.

In situations where a short reagent filling time is desired, the particle collection chamber 240 may be designed having a large width. However, the risk of trapping bubbles in the particle collection chamber 240 may increase with a large width of the channel. Further, a structural stability of the collecting device 200 may be lower with a large width of the channel and hence a large distance between side walls of the channel. Thus, the collecting device 200 may be provide with pillars within the channel. The pillars may extend from the first layer 202 to the second layer 220 and may provide structural stability of the collecting device 200. The pillars may also improve bonding of the first layer 202 to the second layer 220.

Figure 4:
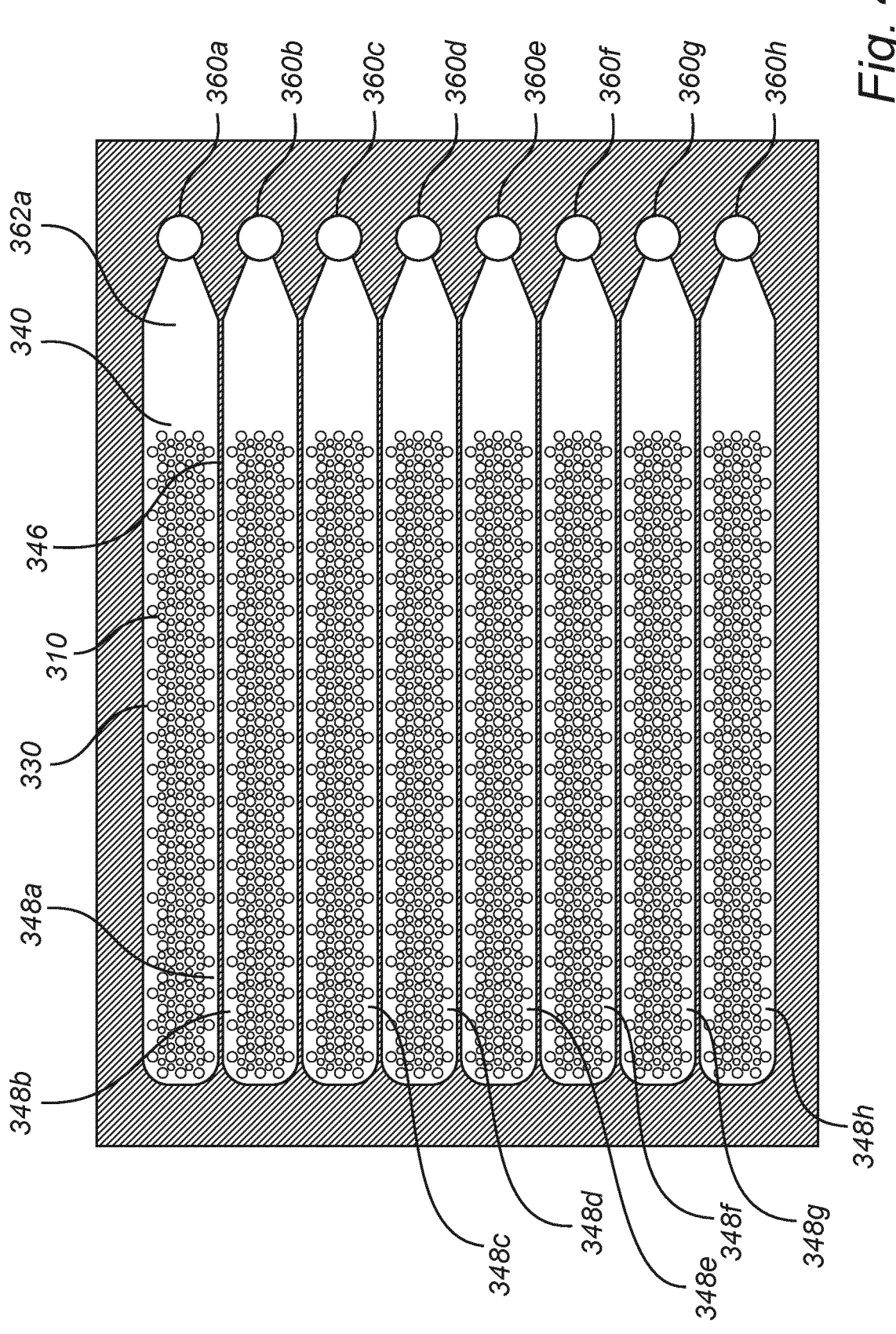

Referring now to FIG. 4, a particle collection chamber 340 according to a second embodiment is shown. The particle collection chamber 340 is formed such that trapping of bubbles in the particle collection chamber 340 during filling of the particle collection chamber 340 with a liquid reagent may be reduced or avoided. Further, the particle collection chamber 340 is formed for facilitating a fast reagent filling time, such as providing a reagent filling time shorter than 10 s, where the particle collection chamber 340 has a size of less than 30 μl or less than 20 μl.

Like FIG. 3, FIG. 4 shows a top view of the particle collection chamber 340 with the first layer and the second layer being removed from the view, whereas the inlets 310 and the outlets 330 are illustrated to indicate the relations between the inlets 310 and the outlets 330 and the particle collection chamber 340. However, lateral walls surrounding the particle collection chamber 340 are indicated in FIG. 3.

The particle collection chamber 340 comprises at least one side wall 346 within an area defined by an outer periphery of the particle collection chamber 340. Thus, the at least one side wall 346 provides guidance of flow of the reagent when the particle collection chamber 340 is filled.

In the embodiment shown in FIG. 4, the side walls 346 completely separate portions of the particle collection chamber 340. Thus, the particle collection chamber 340 is separated into a plurality of compartments 348a-348h. Thus, the side wall 346 indicated in FIG. 4 is arranged such that the compartments 348a, 348b are arranged on opposite sides of the side wall 346.

Thanks to the side wall 346 the flow of the reagent may be guided along a path through the particle collection chamber 340. In particular, the flow of the reagent may be guided to flow along the side wall 346 in each compartment 348a, 348b such that the flow of the reagent propagates along a main direction of a channel defined by the respective compartment 348a, 348b.

Thanks to the particle collection chamber 340 being separated into a plurality of compartments 348a-348h, the channel in each compartment 348a-348h can simply be arranged to have a larger length in the main direction of propagation of the reagent than width transverse to the main direction. This implies that the reagent may easily fill the width transverse to the main direction as the reagent flows along the length of the channel. This implies that there is a low risk for bubbles being trapped within the particle collection chamber 340 at sides of the channel. Further, thanks to the particle collection chamber 340 having a plurality of compartments 348a-348h, the compartments 348a-348h may be simultaneously filled. Each compartment 348a-348h is relatively small such that it may be quickly filled. Since all compartments 348a-348h may be filled simultaneously, the reagent filling time of the particle collection chamber 340 may also be very short, such as shorter than 10 s.

In FIG. 4, a plurality of liquid access ports 360a-360h are shown. Each liquid access port 360a-360h is associated with a corresponding unique compartment 348a-348h of the particle collection chamber 340.

Thus, the compartments 348a-348h of the particle collection chamber 340 may each be supplied through a dedicated liquid access port 360a-360h. Thus, there is an accurate control of supply of reagent to the respective compartments 348a-348h, since each compartment 348a-348h is individually supplied. The compartments 348a-348h may be filled simultaneously for providing a very fast filling of the entire particle collection chamber 340. Also, the compartments 348a-348h may be filled in different manners such as at different times or by providing different reagents to different compartments 348a-348h.

However, it should be realized that a single liquid access port may alternatively be used, wherein the single liquid access port may branch for feeding reagent into all of the plurality of compartments 348a-348h. Thus, a simple manner of simultaneously filling all of the plurality of compartments 348a-348h may be provided.

According to yet another alternative, plural liquid access ports may be used, wherein each liquid access port feeds reagent into a subset of the compartments 348a-348h, wherein the subset comprises more than one compartment. Thus, filling of each compartment 348a-348h is not individually controlled. However, there is a possibility of different handling for different subsets of the compartments 348a-348h.

Each of the liquid access ports 360a-360h may be arranged at or close to the outer periphery of the particle collection chamber 340. Since the liquid reagent may thus enter the particle collection chamber 340 close to the periphery of the particle collection chamber 340, the liquid reagent is limited by the periphery of the particle collection chamber 340 from propagating in any direction from the point of entry. The compartments 348a-348h may define narrow channels such that the reagent enters each compartment 348a-348h at a short end of the channel and may propagate along the channel for filling the compartment 348a-348h. Thus, flow of the reagent when filling the particle collection chamber 340 can be further controlled and a risk for bubbles being trapped in the particle collection chamber 340 is further reduced.

As shown in FIG. 4, the liquid access ports 360a-360h may end outside the outer periphery of the particle collection chamber 340 in the plane of the particle collection chamber 340. The liquid access ports 360a-360h may be connected by short connecting channels (only channel 362a, 362h are shown for better visibility of FIG. 4) connecting each of the liquid access ports 360a-360h into the particle collection chamber 340 at the periphery of the particle collection chamber 340. Thus, the short connecting channels 362a, 362h may transport the reagent from the respective liquid access ports 362a, 362h to the particle collection chamber 340.

Like in the embodiment of FIG. 3, the particle collection chamber 340 with the inlets 310 and outlets 330 may be sealed as soon as the particles (which may carry an infectious disease) have been collected. Still, the reagent may be provided into the particle collection chamber 340 through the liquid access ports 360a-360h and the connecting channels 362a, 362h, which may be sealed when the reagent has been provided.

The liquid access ports 360a-360h may be configured to extend through the first layer 202 or the second layer 220. The liquid access ports 360a-360h may be arranged on the same side such that the liquid access ports 360a-360h extend through the same layer, e.g. the first layer 202.

The liquid access ports 360a-360h may be configured to draw reagent into the liquid access ports 360a-360h by a capillary force. Thus, the liquid access ports 360a-360h may have a cross-sectional size, such as a cross-sectional diameter that is sufficiently small for the reagent to be drawn into the particle collection chamber 340.

The inlets 310 and outlets 330 may function as openings of the particle collection chamber 340 through which air in the particle collection chamber 340 may escape when the particle collection chamber 340 is filled by the reagent. The plurality of inlets 310 and the plurality of outlets 330 may be distributed over the area of the particle collection chamber 340, which may provide a high efficiency of particle collection and reduce a risk for bubbles being trapped in the particle collection chamber 340.

The inlets 310 and the outlets 330 may be configured to draw reagent from the particle collection chamber 340 into the inlets 310 and outlets 330 by a capillary force. Thus, the inlets 310 and the outlets 330 may have a cross-sectional size, such as a cross-sectional diameter that is sufficiently small for the reagent to be drawn into the inlets 310 and the outlets 330.

Referring now to FIG. 5, a method for collection of airborne particles exhaled by a human being and providing a reagent to the collected particles will be described.

The method comprises receiving 402 a flow of air 104 from a human being onto a plurality of inlets 210, 310 of a collecting device 200. The method further comprises passing 404 the flow of air 104 through the inlets 210, 310 into a particle collection chamber 240, 340.

The plurality of inlets 210, 310 may extend through at least a first layer 202. The flow of air 104 may thus be received on a surface forming an interface between the collecting device 200 and an external environment outside the collecting device 200, e.g. an internal space in a sampling compartment of a sample collector 100. The flow of air 104 is passed by the plurality of inlets 210, 310 from the external environment outside the collecting device 200 into the particle capturing chamber 240, 340. The particle capturing chamber 240, 340 may be defined between the first layer 202 and a second layer 220 of the collecting device 200 spaced apart from the first layer 202.

The method further comprises capturing 406 airborne particles in the flow of air 104 entering the particle collection chamber 240, 340 by impaction of airborne particles on a first surface 222 of the second layer 220. The method further comprises passing 408 the flow of air 104 out of the particle collection chamber 240, 340 through outlets 230, 330 extending through at least the second layer 220 of the collecting device 200 to an external environment outside the collecting device 200.

The inlets 210, 310 and the outlets 230, 330 may be staggered such that the center axes of the inlets 210, 310 are displaced from the center axes of the outlets 230, 330 and the center axes of the inlets 210, 310 and the outlets 230, 330 are not aligned. Thus, ends 214 of the inlets 210, 310 are configured to face the first surface 222 of the second layer 220, such that particles are captured at the first surface 222 between the outlets 230, 330. The method thus causes the flow of air 104 to be forced to change direction, such that momentum of particles having a certain size will cause the particles not to follow the flow of air 104 in its change of direction and instead the particles will be captured on the first surface 222.

The method further comprises filling 410 the particle collection chamber 240, 340 with a reagent through at least one liquid access port 260a-260b, 360a-360h, wherein the reagent is guided to flow through the particle collection chamber 240, 340 along at least one side wall 246, 346 through portions of the particle collection chamber 240, 340 on opposite sides of the at least one side wall 246, 346.

Thus, the flow of reagent is controlled within the particle collection chamber 240, 340 such that a risk of bubbles being trapped within the particle collection chamber 240, 340 during filling of the particle collection chamber 240, 340 is reduced. Further, the portions of the particle collection chamber 240, 340 may be simultaneously filled for providing a short reagent filling time.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, it should be realized that compartments of the particle collection chamber need not define straight channels but may rather define non-straight paths of propagation of the reagent through the respective compartments when the particle collection chamber is filled by the reagent.

The invention claimed is:

1. A collecting device for collection of airborne particles exhaled by a human being, said collecting device comprising:

a first layer and a second layer, wherein the first layer and the second layer are arranged to be spaced apart for forming a particle collection chamber between the first and the second layer, wherein the first layer comprises a plurality of inlets configured to extend through the first layer for transporting a flow of air therethrough into the particle collection chamber;

wherein ends of the inlets are configured to face a first surface of the second layer for capturing airborne particles in the flow of air entering the particle collection chamber through the ends of the inlets by impaction of airborne particles on the first surface of the second layer;

wherein the second layer comprises a plurality of outlets configured to extend through the second layer for transporting the flow of air therethrough out of the particle collection chamber;

the collecting device further comprising at least one liquid access port for filling the particle collection chamber with a reagent; and wherein the particle collection chamber comprises at least one side wall extending from the first layer to the second layer for defining flow of the reagent through the particle collection chamber when filling the particle collection chamber, such that a first portion of the particle collection chamber and a second portion of the particle collection chamber are arranged on opposite sides of the at least one side wall.

2. The collecting device according to claim 1, wherein the particle collection chamber extends in an area of a plane parallel to the first layer and wherein the at least one liquid access port is arranged at or close to a periphery of the area.

3. The collecting device according to claim 2, wherein the plurality of inlets and the plurality of outlets are distributed over the area of the particle collection chamber.

4. The collecting device according to claim 1, wherein the particle collection chamber is configured for guiding propagation of the reagent from the at least one liquid access port through the particle collection chamber along the at least one side wall, wherein the reagent is guided through a channel having a larger length in a main direction of propagation of the reagent than width transverse to the main direction.

5. The collecting device according to claim 1, wherein the particle collection chamber is separated by the at least one side wall into a plurality of separate compartments, such that the first portion and the second portion form a first compartment and a second compartment, respectively.

6. The collecting device according to claim 5, wherein the collecting device comprises a plurality of liquid access ports, each liquid access port being associated with a unique compartment of the particle collection chamber.

7. The collecting device according to claim 5, wherein the collecting device comprises a single liquid access port for filling each of the plurality of compartments of the particle collection chamber.

8. The collecting device according to claim 1, wherein the at least one side wall is configured to define a non-straight path of propagation of the reagent from the at least one liquid access port through the particle collection chamber.

9. The collecting device according to claim 8, wherein the non-straight path is meander-shaped.

10. The collecting device according to claim 1, wherein the at least one liquid access port has cross-sectional dimensions for allowing the reagent to be passed through the at least one liquid access port into the particle collection chamber by a capillary force.

11. The collecting device according to claim 1, wherein the at least one liquid access port is configured to extend through the first layer or the second layer.

12. The collecting device according to claim 1, wherein the inlets and the outlets have dimensions for allowing the inlets and the outlets to be filled by the reagent from the particle collection chamber by a capillary force, wherein the capillary force further prevents the reagent to escape from the inlets and the outlets.

13. The collecting device according to claim 1, further comprising pillars extending from the first layer to the second layer for improving bonding of the first layer to the second layer.

14. A method for collection of airborne particles exhaled by a human being and providing a reagent to the collected particles, said method comprising:

receiving a flow of air onto a first layer of a collecting device, wherein the first layer comprises a plurality of inlets extending through the first layer;

passing the flow of air through the inlets into a particle collection chamber between the first layer and a second layer of the collecting device spaced apart from the first layer;

capturing airborne particles in the flow of air entering the particle collection chamber by impaction of airborne particles on a first surface of the second layer, wherein ends of the inlets are configured to face the first surface of the second layer;

passing the flow of air out of the particle collection chamber through outlets extending through the second layer of the collecting device;

filling the particle collection chamber with a reagent through at least one liquid access port, wherein the reagent is guided to flow through the particle collection chamber along at least one side wall through a first portion of the particle collection chamber and a second portion of the particle collection chamber on opposite sides of the at least one side wall.

* * * * *